(12) United States Patent
Chaganti et al.

(10) Patent No.: US 11,430,121 B2
(45) Date of Patent: Aug. 30, 2022

(54) ASSESSMENT OF ABNORMALITY REGIONS ASSOCIATED WITH A DISEASE FROM CHEST CT IMAGES

(71) Applicant: Siemens Healthcare GmbH, Erlangen (DE)

(72) Inventors: Shikha Chaganti, Princeton, NJ (US); Sasa Grbic, Plainsboro, NJ (US); Bogdan Georgescu, Princeton, NJ (US); Zhoubing Xu, Plainsboro, NJ (US); Siqi Liu, Princeton, NJ (US); Youngjin Yoo, Princeton, NJ (US); Thomas Re, Monroe, NJ (US); Guillaume Chabin, Paris (FR); Thomas Flohr, Uehlfeld (DE); Valentin Ziebandt, Nuremberg (DE); Dorin Comaniciu, Princeton Junction, NJ (US); Brian Teixeira, Lawrence Township, NJ (US); Sebastien Piat, Lawrence Township, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 30 days.

(21) Appl. No.: 16/837,979

(22) Filed: Apr. 1, 2020

(65) Prior Publication Data
US 2021/0304408 A1 Sep. 30, 2021

Related U.S. Application Data

(60) Provisional application No. 63/002,457, filed on Mar. 31, 2020.

(51) Int. Cl.
*G06T 7/00* (2017.01)
*G06T 7/11* (2017.01)
(Continued)

(52) U.S. Cl.
CPC .............. *G06T 7/0016* (2013.01); *G06T 7/11* (2017.01); *G06T 11/008* (2013.01); *A61B 5/055* (2013.01);
(Continued)

(58) Field of Classification Search
None
See application file for complete search history.

(56) References Cited

U.S. PATENT DOCUMENTS

| 7,196,328 B1 | 3/2007 | Kley | |
| 8,731,255 B2 * | 5/2014 | El-Baz | G06T 7/33 |
| | | | 382/128 |

(Continued)

FOREIGN PATENT DOCUMENTS

RU 2637171 C1 * 11/2017

OTHER PUBLICATIONS

Machine translation of RU-2637171-C1 (Year: 2017).*
(Continued)

*Primary Examiner* — Vu Le
*Assistant Examiner* — Courtney Joan Nelson

(57) ABSTRACT

Systems and methods for assessing a disease are provided. Medical imaging data of lungs of a patient is received. The lungs are segmented from the medical imaging data and abnormality regions associated with a disease are segmented from the medical imaging data. An assessment of the disease is determined based on the segmented lungs and the segmented abnormality regions. The disease may be COVID-19 (coronavirus disease 2019) or diseases, such as, e.g., SARS (severe acute respiratory syndrome), MERS (Middle East respiratory syndrome), or other types of viral and non-viral pneumonia.

20 Claims, 9 Drawing Sheets

(51) Int. Cl.
G06T 11/00 (2006.01)
A61B 5/055 (2006.01)
A61B 6/00 (2006.01)
A61B 8/08 (2006.01)

(52) U.S. Cl.
CPC .......... *A61B 6/5217* (2013.01); *A61B 8/5223* (2013.01); *G06T 2207/10081* (2013.01); *G06T 2207/30061* (2013.01)

(56) References Cited

U.S. PATENT DOCUMENTS

| | | | |
|---|---|---|---|
| 10,039,515 B2* | 8/2018 | Porter | A61K 49/0004 |
| 2004/0086162 A1* | 5/2004 | Doi | G06T 7/0012 |
| | | | 382/131 |
| 2006/0018524 A1* | 1/2006 | Suzuki | G06K 9/6292 |
| | | | 382/128 |
| 2008/0040083 A1* | 2/2008 | Odry | G06T 7/136 |
| | | | 703/2 |
| 2011/0237938 A1* | 9/2011 | Mizuno | G06T 7/187 |
| | | | 600/425 |
| 2019/0050534 A1 | 2/2019 | Apte et al. | |
| 2019/0066281 A1 | 2/2019 | Zheng et al. | |
| 2020/0085382 A1 | 3/2020 | Taerum et al. | |

OTHER PUBLICATIONS

Bernheim et al., "Chest CT findings in coronavirus disease-19 (COVID-19): Relationship to duration of infection", Radiology, 2020, 19 pgs.
Pan et al., "Time course of lung changes on chest CT during recovery from 2019 novel coronavirus (COVID-19) pneumonia", Radiology, 2020, 15 pgs.
Chung et al., "CT imaging features of 2019 novel coronavirus (2019-ncov)", Radiology, 2020, 19 pgs.
Fang et al., "Sensitivity of chest CT for COVID-19: Comparison to RT-PCR", Radiology, 2020, 8 pgs.
Guan et al., "Clinical characteristics of coronavirus disease 2019 in China", New England Journal of Medicine, 2020, 13 pgs.
Hosseiny et al., "Radiology perspective of coronavirus disease 2019 (COVID-19): Lessons from severe acute respiratory syndrome and middle east respiratory syndrome", American Journal of Roentgenology, 2020, 5 pgs.
Yang et al., "Automatic liver segmentation using an adversarial image-to-image network", International Conference on Medical Image Computing and Computer-Assisted Intervention, Springer, 2017, pp. 507-515.
Kanne et al., "Essentials for radiologists on COVID-19: An update—Radiology scientific expert panel", Radiology, 2020, 4 pgs.
Kim, "Outbreak of novel coronavirus (COVID-19): What is the role of radiologists?", European Radiology, 2020, 2 pgs.
Luo et al., "Adaptive gradient methods with dynamic bound of learning rate", arXiv e-prints, page arXiv:1902.09843, Feb. 2019, 1-19 pgs.
Wilson et al., "Case-fatality risk estimates for COVID-19 calculated by using a lag time for fatality", Centers for Disease Control and Prevention,2020, vol. 26, No. 6, 104 pgs.
Xie et al., "Chest CT for typical 2019-ncov pneumonia: Relationship to negative RT-PCT testing", Radiology, 2020, 1-11 pgs.
Zhao et al., "Relation between chest CT findings and clinical conditions of coronavirus disease (COVID-19) pneumonia: A multicenter study", American Journal of Roentgenology, 2020, 1-6 pgs.
Bai et al., "Performance of radiologists in differentiating COVID-19 from viral pneumonia on chest CT", Radiology, 2020, 28 pgs.
Shan et al., "Lung Infection quantification of COVID-19 in CT images with deep learning", arXiv preprint arXiv:2003.04655-, 2020, 19 pgs.
Wang et al. "A deep learning algorithm using CT images to screen for corona virus disease (COVID-19)", medRxiv, 2020, 19 pgs.

Xu et al. "Deep learning system to screen coronavirus disease 2019 pneumonia", arXiv preprint arXiv, 2002.09334, 2020, 1-29 pgs.
Gozes et al. "Rapid AI development cycle for the coronavirus (COVID-19) pandemic: Initial results for automated detection & patient monitoring using deep learning CT image analysis", arXiv preprint arXiv:2003.05037, 2020, 20 pgs.
Ghesu et al., "Multi-scale deep reinforcement learning for real-time 3D-landmark detection in CT scans", IEEE Transactions on Pattern Analysis and Machine Intelligence, 2017, 1-14 pgs.
Ronneberger et al., "U-Net: convolutional networks for biomedical image segmentation", International Conference on Medical Image Computing and Computer-Assisted Intervention, Springer, 2015, pp. 234-241.
Extended European Search Report (EESR) dated Aug. 2, 2021 in corresponding European Patent Application No. 21165531.1.
Shi, Feng et al: "Large-Scale Screening of CVID-19 from Community Acquired Pneumonia using Infection Size-Aware Classification"; (2020); arxiv.org; Cornell University Library.
Fang, Zhenyu et al: "Severity Assessment of Coronavirus Disease 2019 (COVID-19) Using Quantitative Features from Chest CT Images"; (2020); arxiv.org; Cornell Univeristy Library.
Gozes, Ophier et al: "Rapid AI Development Cycle for the Coronavirus (COVID-19) Pandemic: Initial Results for Automated Detection & Patient Monitoring using Deep Learning CT Image Analysis"; (2020); arxiv.org; Cornell University Library; pp. 1-19; XP081619242.
Lang et al., "Hypoxaemia related to COVID-19: vascular and perfusion abnormalities on dual-energy CT", Lancet Infect Dis, Apr. 30, 2020, 3 pgs.
Hong, Xin et al: "Deep Fusion Network for Image Completion";Multimedia, ACM, 2 Penn Plaza, Suite 701, New York, NY 10121-0701 USA; Oct. 15, 2019 (Oct. 15, 2019), pp. 2033-2042, XP058442705.
Siqi, Liu et al: "Decompose to manipulate: Manipulate Object Synthesis in 3D Medical Images with Structured Image Decomposition"; arxiv.org, Cornell University Library, 201 Olin Library Cornel University Ithaca, NY 14853; Dec. 4, 2018 (Dec. 4, 2018); XP081022739.
Wu, Eric et al: "Conditional Infilling GANs for Data Augmentation in Mammogram Classification"; Advences in Intelligent Data Analysis XIX, (Lecture Notes in Computer Science: Lect. Notes Computer); Springer International Publishing, Cham; pp. 98-106,Sep. 12, 2018 (Sep. 12, 2012); XP047526321.
Dakai, Jin et al: "CT-Realistic Lung Nodule Stimulation from 3D Conditional Generative Adversarial Networks for Robust Lung Segmentation"; arxiv.org, Cornell University Library, 201 Olin Library Cornel University Ithaca, NY 14853; Jun. 11, 2018 /Jun. 11, 2018); XP080889390.
Siqi, Lu et al: "3D Tomographic Pattern Synthesis for Enhancing the Quantification of COVID-19"; arxiv.org, Cornell University Ithaca, NY 14853; May 5, 2020 (May 5, 2020); XP081658938.
Pan, Feng et al: "Time course of lung changes at chest CT during recovery from coronavirus disease 2019 (COVID-19)"; Radiology 295.3 (2020); pp. 715-721; https://pubs.rsna.org/doi/full/10.1148/radiol.2020200370.
Li, Guangxu et al: "Statistical shape model building method using surface registration and model prototype." Optics & Laser Technology 110 (2019); pp. 234-238; https://www.sciencedirect.com/science/article/pii/S0030399217311283 (Year: 2019).
Bogdan, Georgescu et al: "Machine Learning Automatically Detects COVID-19 using Chest CTs in a large Multicenter Cohort"; Jun. 11, 2020; XP055858989.
Fang, Mengjie et al: "CT radiomics can help screen the coronavirus disease 2019 (COVID-19): a preliminary study"; Science China; Jul. 2020; vol. 63.
Dilbag Singh et al., ("Classification of COVID-19 patients from chest CT images using multi-objective differential evolution-based convolutional neural networks", Springer, Apr. 27, 2020, pp. 1-11). (Year: 2020).
Fang et al., ("CT radiomics can help screen the coronavirus disease 2019 (COVID-19): a preliminary study", Springer, vol. 63, No. 7, Apr. 15, 2020, pp. 1-8) (Year: 2020).

(56) References Cited

OTHER PUBLICATIONS

Huang, Gao et al; "Densely Connected Convolutional Networks" Proceedings of the IEEE Conference on Computer Vision and Pattern Recognition, pp. 4700-4708, 2017.

Ulyanov, Dmitry et al., "Instance Normalization: The Missing Ingredient for Fast Stylization", Nov. 6, 2017, 6 pp.

Ioffe, Sergey, and Christian Szegedy. "Batch normalization: Accelerating deep network training by reducing internal covariate shift." arXiv preprint arXiv:1502.03167 (2015).

He, Kaiming, et al. "Deep Residual Learning for Image Recognition" Proceedings of the IEEE Conference on Computer Vision and Pattern Recognition, pp. 770-778, 2016.

Nie, Dong et al. "Medical Image Synthesis with Context-Aware Generative Adversarial Networks" arXiv:1612.05362v1 [cs.CV] Dec. 16, 2016.

Nair V. et al.:; "Rectified linear units improve restricted boltzmann machines"; in Proceedings of the 27th international conference on machine learning (ICML-10); pp. 807-814; 2010.

Yang et al., "Class-Aware Adversarial Lung Nodules Synthesis in CT Images", Dec. 28, 2018, 5 pgs.

Jin et al., "CT-Realistic Lung Nodule Simulation from 3D Conditional Generative Adversarial Networks for Robust Lung Segmentation", Jun. 11, 2018, 8 pgs.

"Dong Yang et al: ""Automatic Liver Segmentation Using an Adversarial Image-to-lmage Network""; arxiv.org, Cornell University Library, 201 Olin Library Cornell University Ithaca, NY 14853; XP080779390; DOI: 10.1007/978-3-319-66179-7 58 / Jul. 25, 2017".

Wang et al., "WGAN-Based Synthetic Minority Over-Sampling Technique: Improving Semantic Fine-Grained Classification for Lung Nodules in CT Images", IEEE Access, vol. 7, Jan. 30, 2019, 18450-18463.

Frid-Adar, et al., "GAN-based Synthetic Medical Image Augmentation for Increased CNN Performance in Liver Lesion Classification", Mar. 3, 2018, IEEE, arXiv:1803.01229v1, 11 pgs.

Miyato et al., "Spectral Normalization for Generative Adversarial Networks", ICLR, Feb. 16, 2018, arXiv:1802.05957v1, 27 pgs.

Aberle et al., "The National Lung Screening Trial: Overview and Study Design", Radiology, vol. 258: No. 1, Jan. 2011, 12 pgs.

Xu et al., "Correlation via synthesis: end-to-end nodule image generation and radiogenomic map learning based on generative adversarial network", arXiv preprint arXiv:1907.03728, 2019.

Milletari, Fausto et al.:; "V-Net: Fully Convolutional Neural Networks for Volumetric Medical Image Segmentation", CoRR (ArXiv),vol. abs/1606.04797v1, Jun. 15, 2016 (Jun. 15, 2016), pp. 1-11, XPO55293637.

"Shin Hoo-Chang et al: ""Medical Image Synthesis for Data Augmentation and Anonymization Using Generative Adversarial Networks""; International Conference on Financial Cryptography and Data Security; [Lecture Notes in Computer Science; Lect.Notes Computer]; Springer, Berlin; Heidelberg; pp. 1-11; XP047485123; ISBN: 978-3-642-17318-9; [gefunden am Sep. 12, 2018]; Abstract / Dec. 9, 2018".

John Hopkins University (JHU), "COVID-19 Dashboard Statistics", retrieved online at https://gisanddata.maps.arcgis.com/apps/opsdashboard/index.html, May 1, 2020, 1 pg.

Mizumoto et al., "Estimating the Asymptomatic Proportion of Coronavirus Disease 2019 (COVID-19) Cases on Board the Diamond Princess Cruise Ship, Yokohama, Japan, 2020", Eurosurveillance,vol. 25, No. 10, 2020, pp. 1-5.

Ji et al., "Potential Association Between COVID-19 Mortality and Health-Care Resource Availability", The Lancet Global Health, vol. 8, No. 4, 2020, p. e480.

Emanuel et al., "Fair Allocation of Scarce Medical Resources in the Time of COVID-19", New England Journal of Medicine, 2020, pp. 1-7.

Ai et al., "Correlation of Chest CT and RT-PCR Testing in Coronavirus Disease 2019 (COVID-19) in China: A Report of 1014 Cases", Radiology, 2020, 23 pgs.

Rubin et al., "The Role of Chest Imaging in Patient Management during the COVID-19 Pandemic: A Multinational Consensus Statement from the Fleischner Society", Chest, 2020, pp. 1-24.

Li et al., "Artificial Intelligence Distinguishes COVID-19 from Community Acquired Pneumonia on Chest CT", Radiology, 2020, 16 pgs.

Inui et al., "Chest CT Findings in Cases from the Cruise Ship "Diamond Princess" with Coronavirus Disease 2019 (COVID-19)", Radiology: Cardiothoracic Imaging, 2020, vol. 2, No. 2, 17 pgs.

Chartsias et al., "Adversarial Image Synthesis for Unpaired Multi-Modal Cardiac Data", International Workshop on Simulation and Synthesis in Medical Imaging, Springer, 2017, pp. 1-10.

Wang et al., "Unsupervised Learning for Cross-Domain Medical Image Synthesis using Deformation Invariant Cycle Consistency Networks", International Workshop on Simulation and Synthesis in Medical Imaging, Springer, arXiv e-prints, arXiv:1808.03944v1, Aug. 12, 2018, 10 pgs.

Yang et al., "Unpaired Brain MR-to-CT Synthesis using a Structure-Constrained CycleGAN", in Deep Learning in Medical Image Analysis and Multimodal Learning for Clinical Decision Support, Springer, arXiv e-prints, arXiv:1809.04536v1, Sep. 12, 2018, 8 pgs.

Liu et al., "Decompose to Manipulate Object Synthesis in 3D Medical Images with Structured Image Decomposition", arXiv e-prints, arXiv:1812.01737v2, Feb. 7, 2019, 8 pgs.

Xu et al., "Tunable CT Lung Nodule Synthesis Conditioned on Background Image and Semantic Features", International Workshop on Simulation and Synthesis in Medical Imaging, Springer, 2019, pp. 62-70.

Gao et al., "Augmenting LIDC Dataset Using 3D Generative Adversarial Networks to Improve Lung Nodule Detection", Medical Imaging 2019: Computer-Aided Diagnosis, International Society for Optics and Photonics, 2019, vol. 10950, pp. 1-10.

Han et al., "Synthesizing Diverse Lung Nodules Wherever Massively: 3D Multi-Conditional GAN-based CT Image Augmentation for Object Detection", International Conference on 3D Vision (3DV), IEEE, arXiv e-prints, arXiv:1906.04962, Aug. 12, 2019, 9 pgs.

Liu et al., "No Surprises: Training Robust Lung Nodule Detection for Low-Dose CT Scans by Augmenting with Adversarial Attacks", arXiv e-prints, arXiv:2003.03824, Mar. 8, 2020, 10 pgs.

Cohen et al., "Distribution Matching Losses Can Hallucinate Features in Medical Image Translation", International Conference on Medical Image Computing and Computer-Assisted Intervention, Springer, arXiv e-prints, arXiv: 1805.0884, May 22, 2018, pp. 1-11.

Vollmer et al., "Improved Laplacian Smoothing of Noisy Surface Meshes", Computer Graphics Forum, The Eurographics Association and Blackwell Publishers, vol. 18 , No. 3, 1999, 8 pgs.

Stolte et al., "Novel Techniques for Robust Voxelization and Visualization of Implicit Surfaces", Graphical Models, 2001, vol. 63, pp. 387-412.

Loshchilov et al., "Decoupled Weight Decay Regularization", arXiv e-prints, arXiv: 1711.05101, Jan. 4, 2019, pp.1-19.

Chaganti et al., "Quantification of Tomographic Patterns Associated with COVID-19 from Chest CT", arXiv e-prints, arXiv:2004.01279, Apr. 2020, 24 pgs.

Regan et al., "Genetic Epidemiology of COPD (COPDGene) Study Design", COPD: Journal of Chronic Obstructive Pulmonary Disease, vol. 7, No. 1, 2011, pp. 1-10.

Chaganti, Shikha et al. "Quantification of Tomographic Patterns Associated with COVID-19 from Chest CT", 2020, https://arxiv.org/ftp/arxiv/papers/2004/2004.01279.pdf.

Mei et al., "Artificial intelligence-enabled rapid diagnosis of COVID-19 patients", medRxiv preprint doi: https://doi.org/10.1101/2020.04.12.20062661, May 7, 2020, 30 pgs.

Bai et al., "AI Augmentation of Radiologist Performance in Distinguishing COVID-19 from Pneumonia of Other Etiology on Chest CT", Radiology, 2020, 29 pgs.

Singh et al., "Classification of COVID-19 patients from chest CT images using multi-objective differential evolution-based convolutional neural networks", European Journal of ClinicalMicrobiology & Infectious Diseases; https://doi.org/10.1007/s10096-020-03901-z, Apr. 27, 2020, 11 pgs.

(56) References Cited

OTHER PUBLICATIONS

Jhu, Coronavirus COVID-19 Global Cases by the Center for Systems Science and Engineering (CSSE) at Johns Hopkins University (JHU), https://gisanddata. maps, arcgis. com, Mar. 15, 2020.

Simpson et al., "Radiological Society of North America Expert Consensus Statement on Reporting Chest CT Findings Related to COVID-19, Endorsed by the Society of Thoracic Radiology, The American College of Radiology, and RSNA", Radiol Cardiothorac Imaging ,2020, vol. 2, No. 2, 24 pgs.

Müllner, "Modern hierarchical, agglomerative clustering algorithms", arXiv PreprarXiv11092378, Sep. 12, 2011, 29 pgs.

Waskom, "Seaborn: statistical data visualization", Python 2.7 and 3.5.

Friedman, "Greedy Function Approximation: A Gradient Boosting Machine", The Annals of Statistics, 2001, vol. 29, No. 5, pp. 1189-1232.

Prokop et al., "CO-RADS—A categorical CT assessment scheme for patients with suspected COVID-19: definition anti evaluation", Radiology, 2020, 37 pgs.

Carter et al., "ROC-ing along: Evaluation and interpretation of receiver operating characteristic curves", Surgery, 2016, vol. 159, No. 6, pp. 1-8.

Grillet et al., "Acute pulmonary embolism associated with COVID-19 pneumonia detected by pulmonary CT angiography", Radiology, 2020, 8 pgs.

* cited by examiner

500

|  | Training | Testing |
|---|---|---|
| # Data Sets | Total: 8792 | Total: 27, COVID-19: 15, Normal: 12 |
| Data Origin | Multiple clinical sites including sites in USA, France and Germany | Multiple clinical sites including sites in USA, China, France, and Germany |
| Sex | Female: 3861, Male: 4484, Unknown: 447 | Female: 3, Male: 3, Unknown: 13 |
| Age | Median: 57 years, IQR: 45-66 years, Unknown: 4695 | Median: 59 years, IQR: 46-62, Unknown: 19 |
| Manufacturer | Siemens: 4334, GE: 3380, Philips: 518, Toshiba: 1, Other: 359 | Siemens: 9, UIH: 10, GE: 4, Other: 1 |
| Slice Thickness [mm] | < 1.5: 8467; (1.5, 3.0]: 217; > 3.0: 108 | < 1.5: 24; (1.5, 3.0]: 0; > 3.0: 0 |
| Reconstruction kernel | Soft: 8362; Hard: 70; Unknown: 360 | Soft: 19; Hard: 4 ; Unknown: 1 |

| | Training | Testing |
|---|---|---|
| # Data Sets | Total: 322, COVID-19: 0, Viral Pneumonia: 54, ILD: 268 | Total: 27, COVID-19: 15, Normal: 12 |
| Data Origin | Multiple clinical sites including sites in USA, France and Germany | Multiple clinical sites including sites in USA, China, France, and Germany |
| Sex | Female: 32, Male: 38, Unknown: 232 | Female: 3, Male: 3, Unknown: 13 |
| Age | Median: 68 years, IQR: 62-73.5, Unknown: 278 | Median: 59 years, IQR: 46-62, Unknown: 19 |
| Manufacturer | Siemens: 27, GE: 81, Philips: 3, Toshiba: 1, Other: 114 | Siemens: 9, UIH: 10, GE: 4, Other: 1 |
| Slice Thickness [mm] | $\leq 1.5$: 51; (1.5, 3.0]: 165; $> 3.0$: 86 | $\leq 1.5$: 24; (1.5, 3.0]: 0; $> 3.0$: 0 |
| Reconstruction kernel | Soft: 83; Hard: 26; Unknown: 193 | Soft: 19; Hard: 4; Unknown: 1 |

ASSESSMENT OF ABNORMALITY REGIONS ASSOCIATED WITH A DISEASE FROM CHEST CT IMAGES

CROSS-REFERENCE TO RELATED APPLICATIONS

This application claims the benefit of U.S. Provisional Application No. 63/002,457, filed Mar. 31, 2020, the disclosure of which is incorporated herein by reference in its entirety.

TECHNICAL FIELD

The present invention relates generally to the assessment of abnormality regions associated with a disease from chest computed tomography images, and in particular to the assessment of abnormality regions associated with COVID-19 (coronavirus disease 2019).

BACKGROUND

COVID-19 (coronavirus disease 2019) is an infectious disease caused by the severe-acute respiratory symptom coronavirus 2 (SARS-Cov2). Common symptoms of COVID-19 include fever, cough, and difficulty breathing. In severe cases, COVID-19 can cause pneumonia, severe acute respiratory syndrome, and multiple organ failure. In the majority of cases, patients infected with COVID-19 experience mild to moderate symptoms that do not require hospitalization. However, COVID-19 is fatal to a significant percentage of infected patients. Due to the high reproduction number (RO) and the infectious nature of COVID-19, tools for rapid testing and evaluation are important to track and mitigate its spread.

In the current clinical practice, COVID-19 is diagnosed via RT-PCR (reverse transcription polymerase chain reaction). However, the sensitivity of RT-PCR has been found to be as low as 60 to 70%, potentially resulting in false negatives. Additionally, limited availability of RT-PCR test kits has contributed to the undetected spread of COVID-19.

BRIEF SUMMARY OF THE INVENTION

In accordance with one or more embodiments, systems and methods for assessing a disease are provided. Medical imaging data of lungs of a patient is received. The lungs are segmented from the medical imaging data and abnormality regions associated with a disease are segmented from the medical imaging data. An assessment of the disease is determined based on the segmented lungs and the segmented abnormality regions. In one embodiment, the disease may be COVID-19 (coronavirus disease 2019) and the abnormality regions associated with COVID-19 comprise opacities of one or more of ground glass opacities (GGO), consolidation, and crazy-paving pattern. However, the disease may be any other disease, such as, e.g., SARS (severe acute respiratory syndrome), MERS (Middle East respiratory syndrome), other types of viral pneumonia, bacterial pneumonia, fungal pneumonia, mycoplasma pneumonia, and other types of pneumonia.

In one embodiment, the assessment of the disease is determined by calculating a percent of opacity metric based on a volume of the lungs determined from the segmented lungs and a volume of the abnormality regions determined from the segmented abnormality regions. In another embodiment, the assessment of the disease is determined by calculating a percent of opacity metric for each lobe of the lungs based on a volume of each lobe determined from the segmented lungs and a volume of abnormality regions in each lobe determined from the segmented abnormality regions, assigning each lobe with a score based on its percent of opacity metric, and summing the scores to calculate a lung severity score.

In one embodiment, the assessment of the disease is determined by evaluating a progression of the disease based on a volume of the abnormality regions determined from the segmented abnormality regions, a volume of the lungs determined from the segmented lungs, and a volume of the abnormality regions determined from prior medical imaging data acquired at a previous point in time than the medical imaging data, and a volume of the lungs determined from the prior medical imaging data. In another embodiment, the assessment of the disease is determined by calculating a metric quantifying the disease based on the segmented lungs and the segmented abnormality regions and comparing the calculated metric with a metric quantifying the disease calculated based on prior medical imaging data acquired at a point in time prior to acquisition of the medical imaging data.

In one embodiment, the assessment of the disease is determined by classifying the disease as being one of viral pneumonia, bacterial pneumonia, fungal pneumonia, mycoplasma pneumonia, or other pneumonia. Further viral pneumonia classification can be further sub-divided as COVID-19, SARS, MERS and other forms of viral pneumonia. In another embodiment, the assessment of the disease is determined by detecting presence of COVID-19 in the lungs based on the segmented lungs, the segmented abnormality regions, and patient data.

These and other advantages of the invention will be apparent to those of ordinary skill in the art by reference to the following detailed description and the accompanying drawings.

BRIEF DESCRIPTION OF THE DRAWINGS

FIG. 5 shows a table of details of a dataset used for training and testing a network for the segmentation of lungs, in accordance with one or more embodiments;

FIG. 6 shows a table of details of a dataset used for training and testing a network for the segmentation of abnormality regions, in accordance with one or more embodiments;

DETAILED DESCRIPTION

The present invention generally relates to methods and systems for the assessment of abnormality regions associated with COVID-19 (coronavirus disease 2019) from chest CT (computed tomography) images. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

COVID-19 is an infectious disease that typically presents such respiratory symptoms as fever, cough, and difficulty breathing. CT imaging of the lungs of patients that have COVID-19 show abnormal radiographic regions. The extent of such abnormal radiographic regions correlate to the severity of COVID-19. Embodiments described herein provide for the automated detection and assessment of abnormal radiographic regions commonly present in COVID-19 to thereby evaluate COVID-19 in patients. Advantageously, the detection and assessment of such abnormal radiographic regions in accordance with embodiments described herein provide insight for prognosis prediction, risk prioritization, and therapy response for patients suspected or confirmed as having COVID-19.

It should be understood that while embodiments described herein are described with respect to the assessment of COVID-19 in patients, such embodiments are not so limited. Embodiments may be applied for the assessment of any disease, such as, e.g., other types of viral pneumonia (e.g., SARS (severe acute respiratory syndrome), MERS (Middle East respiratory syndrome), etc.), bacterial pneumonia, fungal pneumonia, mycoplasma pneumonia, and other types of pneumonia.

Figure 1:
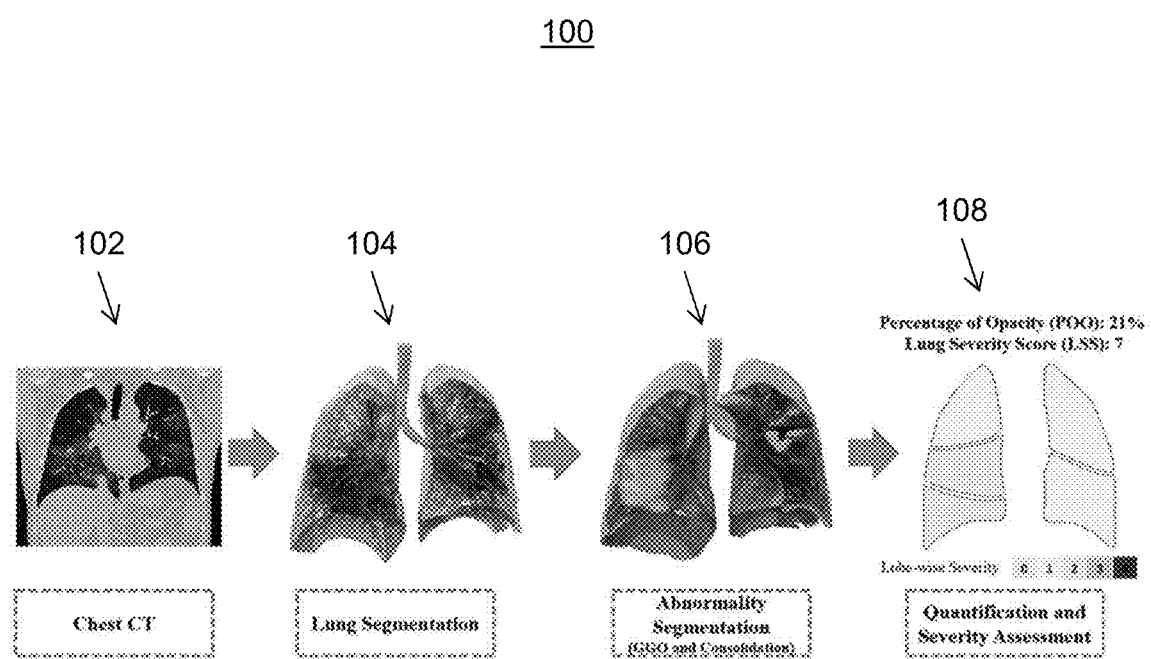
FIG. 1 shows framework for assessing COVID-19 (coronavirus disease 2019) in a patient, in accordance with one or more embodiments.

FIG. 1 shows a framework 100 for assessing COVID-19 in a patient, in accordance with one or more embodiments. In framework 100, a chest CT 102 of lungs of the patient is received as input. A lung segmentation 104 is generated by segmenting the lungs from chest CT 102 and an abnormality segmentation 106 is generated by segmenting abnormality regions associated with COVID-19 from chest CT 102. The abnormality regions associated with COVID-19 may include, e.g., opacities such as GGO (ground glass opacity), consolidation, crazy-paving pattern, etc. An assessment 108 of COVID-19 is determined based on lung segmentation 104 and abnormality segmentation 106. As shown in framework 100, assessment 108 depicts a lobe-wise severity of the lungs and quantifies the severity of COVID-19 according to a POO (percent of opacity) metric and an LSS (lung severity score) metric. In some embodiments, assessment 108 may also determine an assessment of the progression of COVID-19, differentiate COVID-19 from other types of diseases to classify the abnormality regions as being associated with COVID-19, and detect the presence of COVID-19 to diagnose a patient. Further details of framework 100 are described below with respect to FIGS. 2 and 3.

Figure 2:
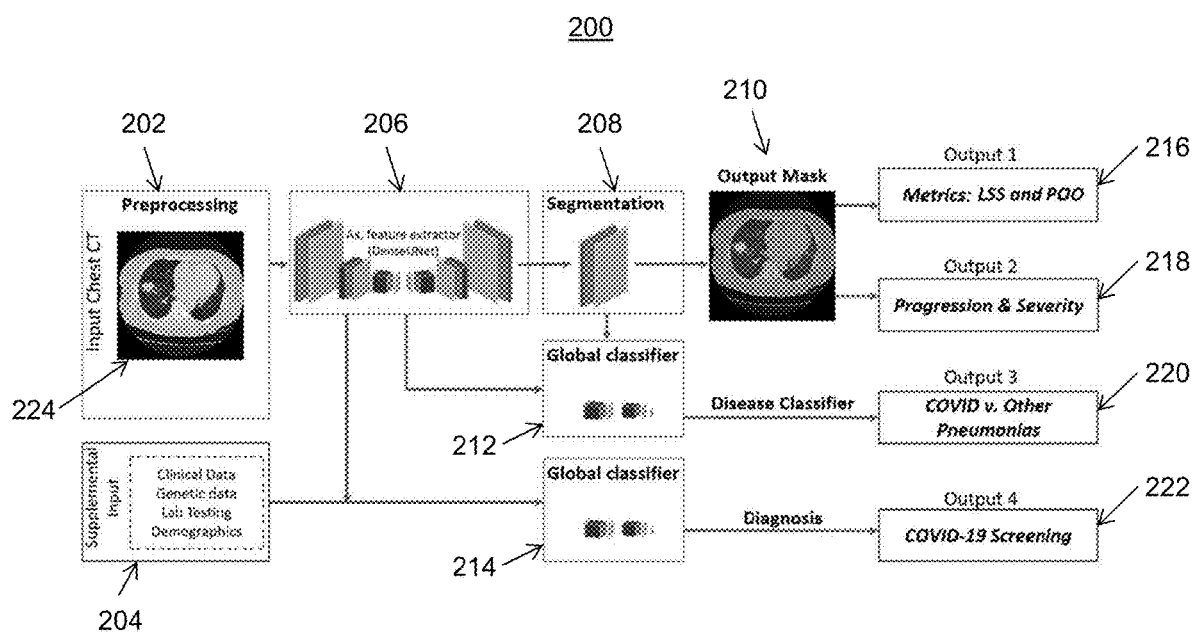
FIG. 2 shows a workflow for assessing COVID-19 in a patient, in accordance with one or more embodiments.
Figure 3:
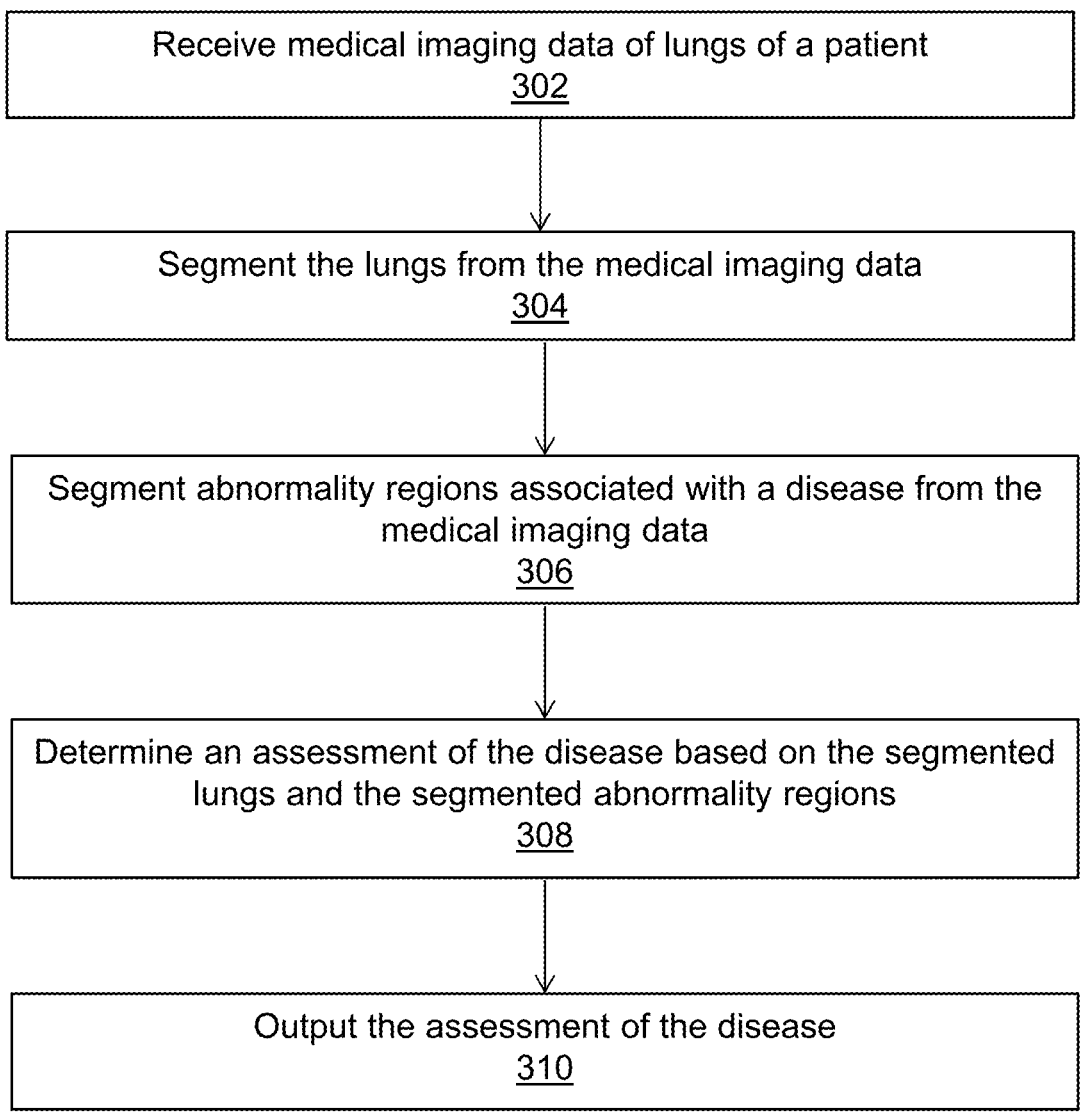
FIG. 3 shows a method for assessing a disease in a patient, in accordance with one or more embodiments.

FIG. 2 is a workflow 200 for assessing COVID-19 in a patient, in accordance with one or more embodiments. FIG. 3 is a method 300 for assessing a disease in a patient, in accordance with one or more embodiments. FIGS. 2 and 3 will be discussed simultaneously with continued reference to FIG. 1. The steps of method 300 may be performed by one or more suitable computing devices, such as computer 902 of FIG. 9.

At step 302, medical imaging data of lungs of a patient is received. In one embodiment, the medical imaging data is CT medical imaging data. For example, the medical imaging data may be chest CT image 102 of FIG. 1 or input chest CT image 224 of FIG. 2. However, the medical imaging data may be of any suitable modality, such as, e.g., MRI (magnetic resonance imaging), ultrasound, x-ray, or any other modality or combination of modalities. The medical imaging data may comprise one or more 2D images or 3D volumes. The medical imaging data may be received directly from an image acquisition device, such as, e.g., a CT scanner, as the medical imaging data is acquired, or can be received by loading a previously acquired medical imaging data from a storage or memory of a computer system or receiving a medical imaging data that has been transmitted from a remote computer system.

In one embodiment, patient data may also be received. In one example, the patient data is supplemental input 204 of FIG. 2. The patient data may include any data relating to the patient, such as, e.g., clinical data, genetic data, lab testing data, demographics data, etc.

At step 304, the lungs are segmented from the medical imaging data. In one example, the lungs are segmented at preprocessing step 202 of FIG. 2 and the segmented lungs may be lung segmentation 104 of FIG. 1.

In one embodiment, the lungs are segmented from the medical imaging data by first detecting anatomical landmarks throughout the medical imaging data using multi-scale deep reinforcement learning. A region of interest (ROI) of the medical imaging data is then extracted based on the detected landmarks. Specifically, the lung ROI is extracted using the detected landmark of the carina bifurcation. Other detected landmarks may additionally or alternatively be utilized. For example, the sternum tip may be used to extract the lung ROI from the medical imaging data where the carina bifurcation is beyond the image field of view of the medical imaging data. The size and the relative location of the lung ROI towards the carina bifurcation (or other detected landmark) are specified according to annotated data. Next, the extracted lung ROI image is resampled to, e.g., a 2 mm isotropic volume and fed into a trained deep image-to-image network (DI2IN) to generate a segmentation mask within the lung ROI. Finally, the segmentation mask is transferred to a unique mask having the same dimension and resolution as the medical imaging data. The unique mask is output as the final lung segmentation mask. The DI2IN is trained during a prior offline or training stage. In one embodiment, the DI2IN is trained on a cohort of patients without the prevalence of viral pneumonia and fine-tuned on another cohort with abnormality regions including consolidation, effusions, masses, etc. to improve the robustness of the lung segmentation over the infected area.

At step 306, abnormality regions associated with a disease are segmented from the medical imaging data. In one embodiment, the disease is COVID-19 and the abnormality regions associated with COVID-19 include opacities such as but not limited to GGO, consolidation, and crazy-paving pattern. Other exemplary diseases include, e.g., other types of viral pneumonia (e.g., SARS, MERS, etc.), bacterial pneumonia, fungal pneumonia, mycoplasma pneumonia, and other types of pneumonia diseases. In one example, abnormality regions are segmented from input chest CT image 224 in FIG. 2 using feature extractor 206 to generate abnormality segmentation 208, which may be overlaid on input chest CT image 224 to generate output mask 210. Feature extractor 206 may be a machine learning based feature extractor, such as, e.g., a DenseUNet. However, any other suitable machine learning based network may be applied for segmenting the abnormality regions. In another example, the segmented abnormality regions may be abnormality segmentation 106 of FIG. 1.

The segmentation of the abnormality regions may be formulated as a semantic segmentation problem involving binary classes. A DenseUNet with anisotropic kernels is trained to transfer the medical imaging data to a segmentation mask of the same size. All voxels in the lungs that fully or partially comprise GGO, consolidations, or crazy-paving patterns (or any other type of abnormality associated with the disease) are defined as positive voxels. The remainder of the image area within the lungs and the entire area outside the lungs are defined as negative voxels. The DenseUNet is trained in an end-to-end segmentation system. The segmentation mask generated by the DenseUNet is filtered using the segmented lungs to that only the abnormality regions present within the lungs are identified. The filtered segmentation mask is output as the final abnormality mask. The final abnormality mask may be overlaid on the medical imaging data. The DenseUNet is discussed in further detail with respect to FIG. 4 below.

At step 308, an assessment of the disease is determined based on the segmented lungs and the segmented abnormality regions. In one example, the assessment is assessment 108 in FIG. 1 or outputs 216-222 in FIG. 2.

In one embodiment, the assessment of the disease is a quantification of the disease as measured by a metric calculated based on the segmented lungs and the segmented abnormality regions. Exemplary metrics include a POO metric and an LSS metric. In one example, such metrics are shown as assessment 108 in FIG. 1 and output 216 determined from output mask 210 in FIG. 2. The POO metric of the lungs represents the overall spread of the disease relative to the volume of the lungs. The POO metric of the lungs is calculated as the total percent volume of the lungs that is affected by the disease according to Equation (1):

$$POO = 100 \times \frac{\text{volume of the abnormality regions in the lungs}}{\text{volume of the lungs}} \quad \text{Equation (1)}$$

where the volume of the abnormality regions in the lungs is determined as the volume of the segmented abnormality regions and the volume of the lungs is determined as the volume of the segmented lungs. The LSS metric is a cumulative measure of the extent of lung involvement in the disease across each lobe of the lungs. For each lobe, a POO is calculated as the total percent volume of the lobe that is affected by the disease according to Equation (2):

$$POO = 100 \times \frac{\text{volume of the abnormality regions in the lobe}}{\text{volume of the lbe}} \quad \text{Equation (2)}$$

where the volume of the abnormality regions in the lobe is determined as the volume of the segmented abnormality regions for the lobe and the volume of the lobe is determined from the segmented lungs. The lobe is assigned a score between 0 and 4 based on the POO. In one example, the lobe is assigned a score of 0 where the lobe is not affected (i.e., POO is 0%), a score of 1 where the POO is 1-25%, a score of 2 where the POO is 25-50%, a score of 3 where the POO is 50-70%, and a score of 4 where the POO is 75-100%. The scores of each of the five lobes of the lungs is summed to calculate the total LSS, resulting in an LSS score ranging from 0 to 20. An LSS score of 0 indicates that none of the lobes are involved while an LSS score of 20 indicates that all five lobes are severely affected by the disease.

In one embodiment, the assessment of the disease is an evaluation of the progression, severity, and type as the disease progresses over time. In one example, the evaluation of the progression, severity, and type is output 218 in FIG. 2. The distribution of different types of abnormalities is analyzed to output the progression of the disease based on longitudinal scanning. In one embodiment, the progression of the disease is evaluated by performing method 300 a number of times using medical imaging data from different points in time and comparing the assessments of the disease for the different points in time. For example, the volume of the segmented abnormality regions relative to the volume of the segment lungs and its histogram of Hounsfield Units (HU) densities corresponding to the abnormality regions may be compared with a volume of abnormal regions relative to a volume of the lungs determined from the prior medical imaging data and its histogram of HU densities corresponding to abnormality regions, where the prior medical imaging data is acquired at a point in time prior to acquisition of the medical imaging data. In another example, the progression of the disease is evaluated by estimating a variation in a metric (e.g., POO or LSS) quantifying the disease at different points in time. The metric may be determined based on the segmented lungs and the segment abnormality regions or directly from other patient data (received at step 302). In one example, the patient may be imaged at each of the points in time to determine the quantification metric. In one embodiment, the progression of the disease is evaluated by comparing data from two or more points in time through registration of data and background subtraction.

In one embodiment, the assessment of the disease is a classification of the disease (e.g., as being COVID-19, SARS, MERS, etc.) by distinguishing between different diseases. In one example, the classification may be output 220 in FIG. 2 showing the classification of the disease as being COVID-19 as compared to other pneumonias. Global classifier 212 in FIG. 2 is trained with training images of different diseases, such as, e.g., COVID-19, SARS, MERS, and other viral and non-viral pneumonias (e.g., bacterial, fungal, mycoplasma, etc.). During the online or testing stage, global classifier 212 receives features of abnormality regions from feature extractor 206 and abnormality segmentation 208 to generate a classification of the disease as output 220. In one embodiment, the classification of the disease is determined by global classifier 212 based on the volume abnormality regions relative to the volume of the lungs, HU density histogram, texture, and other radiomic features of the abnormalities present in the lungs. In one embodiment, the classification of the disease is determined by global classifier 212 directly from patient data (received at step 302).

In one embodiment, the assessment of the disease is a diagnosis of the disease for screening. In one example, the diagnosis may be output 222 in FIG. 2 for COVID-19 screening. Global classifier 214 in FIG. 2 is trained with imaging data as well as other patient data, such as, e.g., clinical data, genetic data, lab testing, demographics, DNA data, symptoms, epidemiological factors, etc. During the online or testing stage, global classifier 214 receives patient data 204 and features of abnormality regions from feature extractor 206 to generate a diagnosis as output 222. In one embodiment, global classifier 214 estimates the detection of the disease based on the segmented lung, segmented abnormality regions, and features of the abnormality. In another embodiment, global classifier 214 estimates the detection of the disease directed from integrated patient data (e.g., images, DNA, epidemiologic risk, etc.) by feeding all integrated patient data into global classifier 214 trained to detect the presence of the disease. Global classifier 214 may be a neural network, such as, e.g., a Deep Profiler.

At step 310, the assessment of the disease is output. For example, the assessment of the disease can be output by displaying the assessment of the disease on a display device of a computer system, storing the assessment of the disease on a memory or storage of a computer system, or by transmitting the assessment of the disease to a remote computer system.

Advantageously, embodiments described herein provide for automated scoring and evaluation of severity and progression of diseases such as, e.g., COVID-19 to enable prioritization of patients requiring hospitalization or ICU (intensive care unit) admittance. Embodiments may assess the disease at different points in time to evaluate disease progression or response to drugs. Embodiments may differentiate between patients with, e.g., COVID-19 and other types of pneumonia based on the unique abnormality patterns associated with COVID-19. Embodiments may be utilized as a screen tool for diseases such as, e.g., COVID-19 by using imaging data in conjunction with other patient data, increasing the overall sensitivity of detection.

Figure 4:
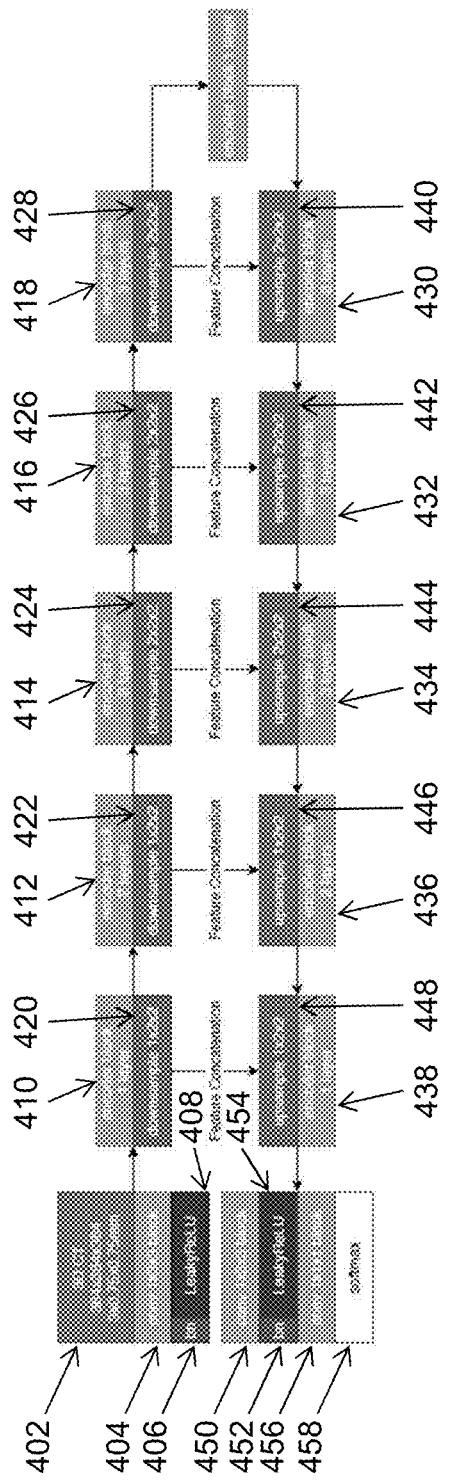
FIG. 4 shows a network architecture of an anisotropic U-Net for segmenting abnormality regions associated with a disease, in accordance with one or more embodiments.

FIG. 4 shows a network architecture 400 of an anisotropic U-Net for segmenting abnormality regions associated with a disease such as, e.g., COVID-19, in accordance with one or more embodiments. Network architecture 400 may be the network architecture of feature extractor 206 of FIG. 2 or the network architecture of the feature extractor applied at step 306 of FIG. 3.

The U-Net is trained using training images resampled to the resolution of 1×1×3 mm. Image intensity is clipped using the standard lung window with the width 1500 HU and level −600 HU before being formalized to [0,1]. The predicted lung masks are used to compute the geometric center of the lungs, then the images are cropped with a fixed bounding box of size 384×384×384. The training images were augmented by perturbing the image intensity with a random interval [−20,20] and then flipping the image in one of the three dimensions by 50% chance. The tensor 3D dimensions are kept in z-y-x order throughout the training and inference stages.

As shown in network architecture 400, a 3D input tensor 402 is fed into a 3D 1×3×3 convolutional layer 404 followed by a batch normalization 406 and a LeakyReLU 408. The features are propagated to encoder blocks 410-416. In encoder blocks 410 and 412, the features are downsampled by a respective 1×2×2 convolution downsampling kernels 420 and 422 with a stride of 1×2×2. The anisotropic downsampling kernels 420 and 422 are designed to preserve the inter-slice resolution of the input tensor 402. Encoder blocks 414-418 have isotropic a respective downsampling kernels 424-428 with a stride of 2×2×2. As shown in FIG. 4, the input to each decoder block 430-438 is obtained by concatenating the output features of the same resolution from encoder block 410-416 and the features upsampled from the previous decoder block 430-438. Upsampling kernels 440-448 are built with transpose convolutional kernels with the sizes and strides the same as their corresponding encoder blocks 410-416. The final network output is derived by projecting the feature maps to a 1×3×3 convolutional layer 450 followed by a batch normalization 452, a LeakyReLU 454, and a 1×1×1 convolutional layer 456, before being activated by softmax activation 458.

The network was trained using the Jaccard index as the training loss function. The loss function $L(p,y)$ between the probability prediction tensor p and the ground truth tensor y is only computed within the precomputed lung segmentation according to Equation (3):

$$L(p, y) = 1 - \frac{p \cdot y + \epsilon}{p \cdot p + t \cdot t - p \cdot t + \epsilon} \quad \text{Equation (3)}$$

where $\epsilon=1$ is the smoothing factor and · represents the tensor inner product operator. the loss function is optimized using Adabound with an initial learning rate of 0.001.

Embodiments described herein were experimentally validated for assessing COVID-19 in patients.

The network for the segmentation of lungs was trained and tested on datasets detailed in table 500 of FIG. 5. For training, the ground truth for each training data set was generated by expert users with a custom annotation tool The user could load the anonymized 3D CT series (volume), interact with the image (including 3 multi-planar reformatted images), draw and edit contours, and mark regions with a specific label for each of the lung lobes that was pre-specified. The final mask was saved as a file together with the reference to the original anonymized CT series. The annotations were reviewed standardized quality guidelines. Each annotation as reviewed by a second, more experienced user. For testing, the ground truth was generated using the same approach as the training data, however the final review was performed by a board certified radiologist.

The network for the segmentation of abnormality regions was trained and tested on datasets detailed in table 600 of FIG. 6. For training, three groups of datasets were identified: 1) COVID-19 datasets, 2) atypical pneumonia datasets, including SARS, MERS, and other viral pneumonia which have similar presentation to COVID-19 and are used as reasonable proxies in the training dataset, and 3) other interstitial lung diseases (ILDs) that present with GGO and consolidation, which are useful for learning the patterns relevant to COVID-19. The ground truth for each training data set was generated by a radiologist with a custom annotation tool The user could load the anonymized 3D CT series (volume), interact with the image (including 3 multi-planar reformatted images), draw and edit contours, and mark regions with a specific label for the abnormalities related to COVID-19 that was pre-specified. The final mask was saved as a file together with the reference to the original anonymized CT series. The annotations were reviewed according to standardized quality guidelines by a board certified radiologist. For testing, the ground truth was generated using the same approach as the training data, however both the initial annotation and final review was performed by a board certified radiologist. The testing included 15 CT images that were confirmed to have COVID-19 by RT-PCR testing. Besides COVID-19 confirmed patients, the test set included 12 controls of patients with no abnormalities in the lung region.

Analyzing the results, from the predicted infect area segmentation, the total POO was measured in the lungs. The Pearson's Coefficient Correlations between predicted POO values and ground truth measures was computed from 15 COVID-19 positive and 12 control cases. The correlation for the total POO in the lung was 0.94 ($p=2.45\times10^{-11}$).

Figure 7:
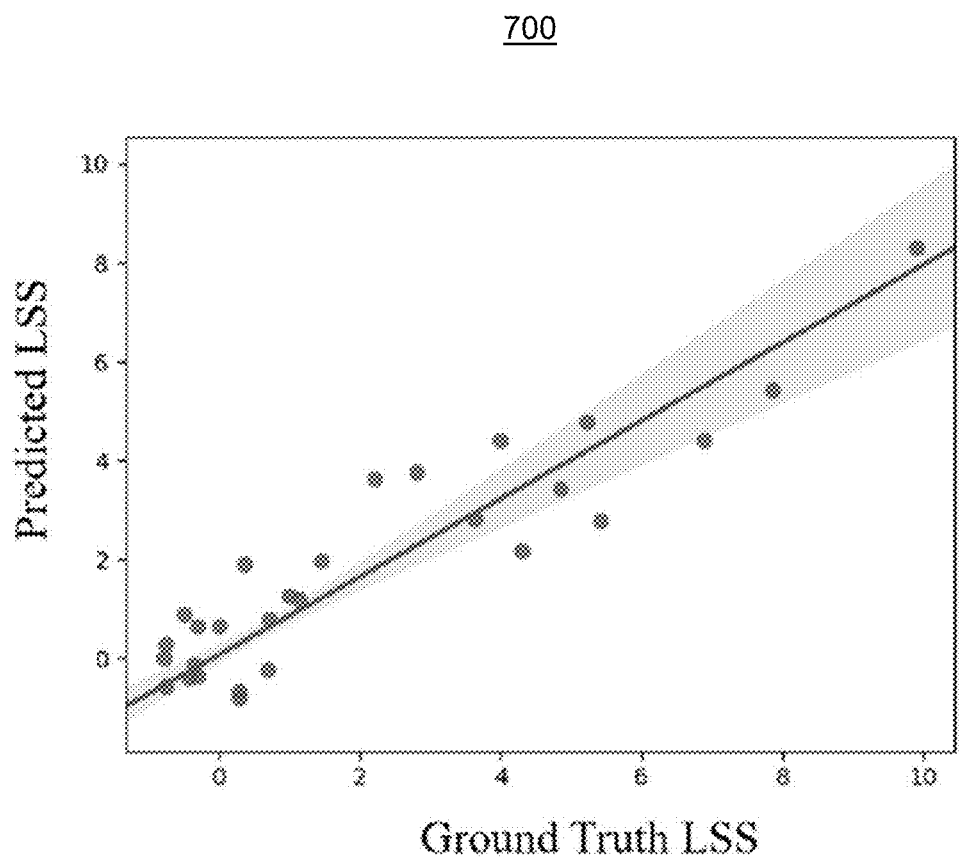
FIG. 7 shows a scatter plot comparing ground truth and predicted lung severity scores, in accordance with one or more embodiments.

FIG. 7 shows a scatter plot 700 between ground truth and predicted LSS. The Pearson's Coefficient Correlations and Kendall-Tau Rank Correlation between predicted severity scores and ground truth measures were computed from 15 COVID-19 positive and 12 control cases. The correlation was 0.94 in both Pearson's Correlation Coefficient and Kendall-Tau Rank Correlation Coefficient ($p=2.35\times10^{-13}$ and $p=7.2\times10^{-9}$ respectively).

Figure 8:
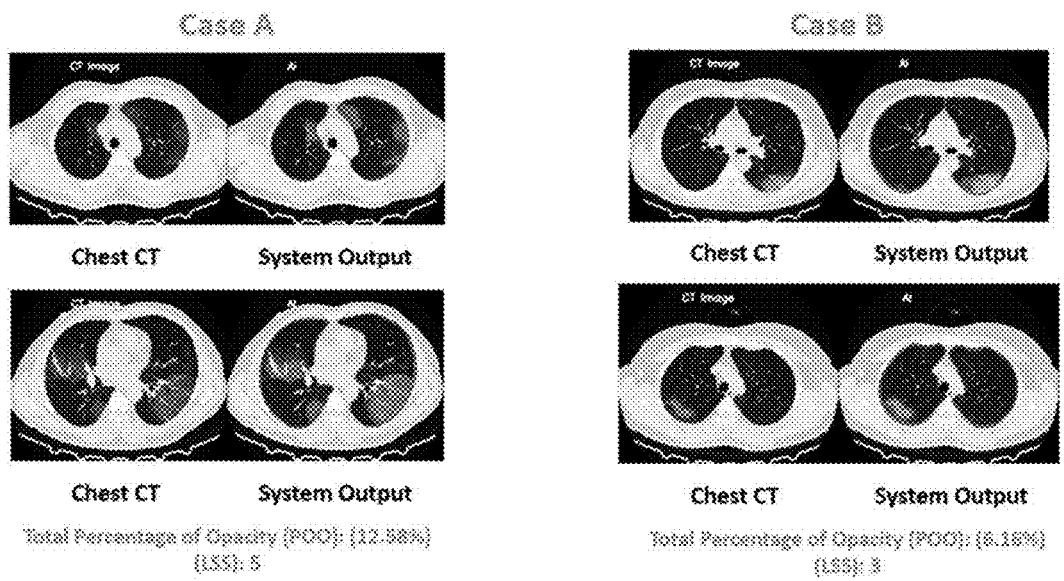
FIG. 8 shows a system output of segmented abnormality regions in accordance with one or more embodiments described herein as compared with an input chest computed tomography image.

FIG. 8 shows a visualization 800 of a system output of segmented abnormality regions in accordance with embodiments described herein as compared with the input chest CT image for Case A and Case B. The POO and LSS are also shown.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 2-3. Certain steps or functions of the methods and workflows described herein, including one or more of the steps or functions of FIGS. 2-3, may be performed by a server or by another processor in a network-based cloud-computing system. Certain steps or functions of the methods and workflows described herein, including one or more of the steps of FIGS. 2-3, may be performed by a client computer in a network-based cloud computing system. The steps or functions of the methods and workflows described herein, including one or more of the steps of FIGS. 2-3, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 2-3, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 9:
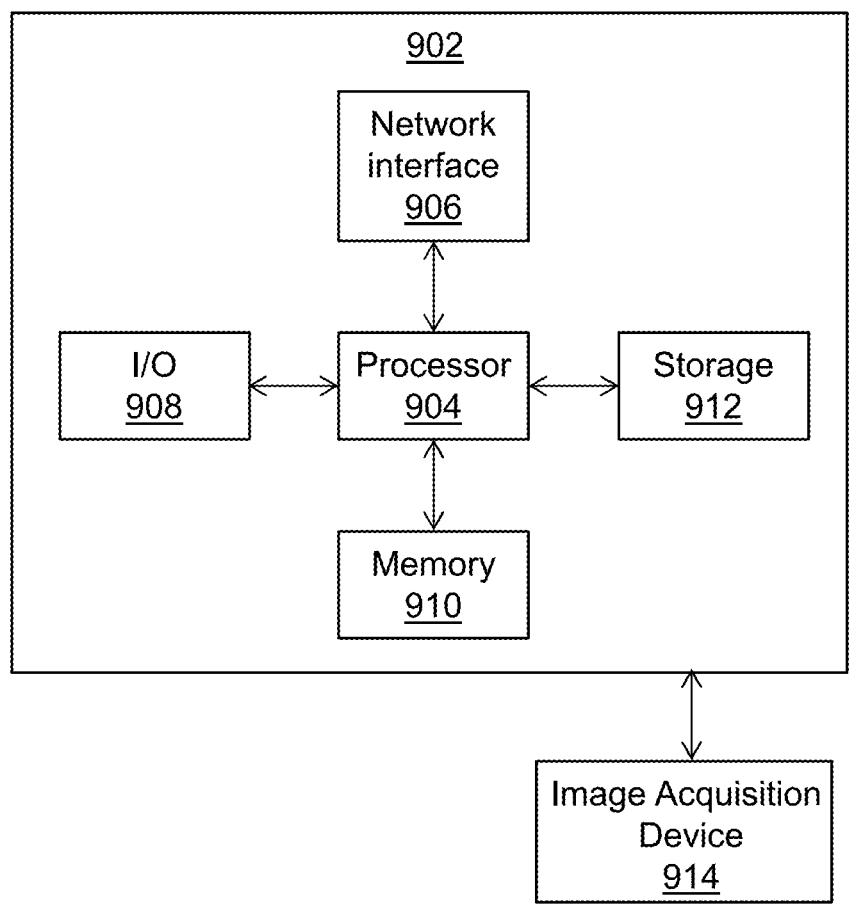
FIG. 9 shows a high-level block diagram of a computer.

A high-level block diagram of an example computer 902 that may be used to implement systems, apparatus, and methods described herein is depicted in FIG. 9. Computer 902 includes a processor 904 operatively coupled to a data storage device 912 and a memory 910. Processor 904 controls the overall operation of computer 902 by executing computer program instructions that define such operations. The computer program instructions may be stored in data storage device 912, or other computer readable medium, and loaded into memory 910 when execution of the computer program instructions is desired. Thus, the method and workflow steps or functions of FIGS. 2-4 can be defined by the computer program instructions stored in memory 910 and/or data storage device 912 and controlled by processor 904 executing the computer program instructions. For example, the computer program instructions can be implemented as computer executable code programmed by one skilled in the art to perform the method and workflow steps or functions of FIGS. 2-4. Accordingly, by executing the computer program instructions, the processor 904 executes the method and workflow steps or functions of FIGS. 2-4. Computer 902 may also include one or more network interfaces 906 for communicating with other devices via a network. Computer 902 may also include one or more input/output devices 908 that enable user interaction with computer 902 (e.g., display, keyboard, mouse, speakers, buttons, etc.).

Processor 904 may include both general and special purpose microprocessors, and may be the sole processor or one of multiple processors of computer 902. Processor 904 may include one or more central processing units (CPUs), for example. Processor 904, data storage device 912, and/or memory 910 may include, be supplemented by, or incorporated in, one or more application-specific integrated circuits (ASICs) and/or one or more field programmable gate arrays (FPGAs).

Data storage device 912 and memory 910 each include a tangible non-transitory computer readable storage medium. Data storage device 912, and memory 910, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 908 may include peripherals, such as a printer, scanner, display screen, etc. For example, input/output devices 908 may include a display device such as a cathode ray tube (CRT) or liquid crystal display (LCD) monitor for displaying information to the user, a keyboard, and a pointing device such as a mouse or a trackball by which the user can provide input to computer 902.

An image acquisition device 914 can be connected to the computer 902 to input image data (e.g., medical images) to the computer 902. It is possible to implement the image acquisition device 914 and the computer 902 as one device. It is also possible that the image acquisition device 914 and the computer 902 communicate wirelessly through a network. In a possible embodiment, the computer 902 can be located remotely with respect to the image acquisition device 914.

Any or all of the systems and apparatus discussed herein, including feature extractor 206, global classifier 212, and global classifier 214 of FIG. 2 and network architecture 400 of FIG. 4, may be implemented using one or more computers such as computer 902.

One skilled in the art will recognize that an implementation of an actual computer or computer system may have other structures and may contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
receiving medical imaging data of lungs of a patient;
segmenting the lungs from the medical imaging data;
segmenting abnormality regions associated with a disease from the medical imaging data;
calculating a volume metric of the lungs based on the segmented lungs;
calculating a volume metric of the abnormality regions based on the segmented abnormality regions; and
determining an assessment of the disease based on the volume metric of the lungs and the volume metric of the abnormality regions, wherein determining an assessment of the disease based on the volume metric of the lungs and the volume metric of the abnormality regions comprises:
calculating a percent of opacity metric by dividing the volume metric of the lungs by the volume metric of the abnormality regions.

2. The method of claim 1, wherein the disease is COVID-19 (coronavirus disease 2019) and the abnormality regions associated with COVID-19 comprise opacities of one or more of ground glass opacities (GGO), consolidation, and crazy-paving pattern.

3. The method of claim 1, wherein determining an assessment of the disease based on the volume metric of the lungs and the volume metric of the abnormality regions further comprises:
evaluating a progression of the disease based on the volume metric of the abnormality regions, the volume metric of the lungs, a volume metric of the abnormality regions determined from prior medical imaging data acquired at a point in time prior to acquisition of the medical imaging data, and a volume metric of the lungs determined from the prior medical imaging data.

4. The method of claim 1, wherein determining an assessment of the disease based on the volume metric of the lungs and the volume metric of the abnormality regions further comprises:
calculating a metric quantifying the disease based on the segmented lungs and the segmented abnormality regions; and
comparing the calculated metric with a metric quantifying the disease calculated based on prior medical imaging data acquired at a previous point in time than the medical imaging data.

5. The method of claim 1, wherein determining an assessment of the disease based on the volume metric of the lungs and the volume metric of the abnormality regions further comprises:
classifying the disease as being one of COVID-19 (coronavirus disease 2019), SARS (severe acute respiratory syndrome), or MERS (middle east respiratory syndrome).

6. The method of claim 1, wherein determining an assessment of the disease based on the volume metric of the lungs and the volume metric of the abnormality regions further comprises:
detecting presence of COVID-19 in the lungs based on the segmented lungs, the segmented abnormality regions, and patient data.

7. The method of claim 1, wherein the disease is a viral pneumonia.

8. A method comprising:
receiving medical imaging data of lungs of a patient;
segmenting the lungs from the medical imaging data;
segmenting abnormality regions associated with a disease from the medical imaging data;
calculating a volume metric of the lungs based on the segmented lungs;
calculating a volume metric of the abnormality regions based on the segmented abnormality regions; and
determining an assessment of the disease based on the volume metric of the lungs and the volume metric of the abnormality regions, wherein determining an assessment of the disease based on the volume metric of the lungs and the volume metric of the abnormality regions comprises:
calculating a percent of opacity metric for each lobe of the lungs based on a volume metric of each lobe determined from the segmented lungs and a volume metric of abnormality regions in each lobe determined from the segmented abnormality regions;
assigning each lobe with a score based on its percent of opacity metric; and
summing the scores to calculate a lung severity score.

9. The method of claim 8, wherein the disease is COVID-19 (coronavirus disease 2019) and the abnormality regions associated with COVID-19 comprise opacities of one or more of ground glass opacities (GGO), consolidation, and crazy-paving pattern.

10. An apparatus comprising:
means for receiving medical imaging data of lungs of a patient;
means for segmenting the lungs from the medical imaging data;
means for segmenting abnormality regions associated with a disease from the medical imaging data;
means for calculating a volume metric of the lungs based on the segmented lungs;
means for calculating a volume metric of the abnormality regions based on the segmented abnormality regions; and
means for determining an assessment of the disease based on the volume metric of the lungs and the volume metric of the abnormality regions, wherein the means for determining an assessment of the disease based on the volume metric of the lungs and the volume metric of the abnormality regions comprises:
means for calculating a percent of opacity metric by dividing the volume metric of the lungs by the volume metric of the abnormality regions.

11. The apparatus of claim 10, wherein the disease is COVID-19 (coronavirus disease 2019) and the abnormality regions associated with COVID-19 comprise opacities of one or more of ground glass opacities (GGO), consolidation, and crazy-paving pattern.

12. The apparatus of claim 10, wherein the means for determining an assessment of the disease based on the volume metric of the lungs and the volume metric of the abnormality regions further comprises:
means for evaluating a progression of the disease based on the volume metric of the abnormality regions, the volume metric of the lungs, a volume metric of the abnormality regions determined from prior medical imaging data acquired at a point in time prior to acquisition of the medical imaging data, and a volume metric of the lungs determined from the prior medical imaging data.

13. An apparatus comprising:
means for receiving medical imaging data of lungs of a patient;
means for segmenting the lungs from the medical imaging data;
means for segmenting abnormality regions associated with a disease from the medical imaging data;
means for calculating a volume metric of the lungs based on the segmented lungs;
means for calculating a volume metric of the abnormality regions based on the segmented abnormality regions; and
means for determining an assessment of the disease based on the volume metric of the lungs and the volume metric of the abnormality regions, wherein the means for determining an assessment of the disease based on the volume metric of the lungs and the volume metric of the abnormality regions comprises:
means for calculating a percent of opacity metric for each lobe of the lungs based on a volume metric of each lobe determined from the segmented lungs and a volume metric of abnormality regions in each lobe determined from the segmented abnormality regions;
means for assigning each lobe with a score based on its percent of opacity metric; and
means for summing the scores to calculate a lung severity score.

14. A non-transitory computer readable medium storing computer program instructions, the computer program instructions when executed by a processor cause the processor to perform operations comprising:
receiving medical imaging data of lungs of a patient;
segmenting the lungs from the medical imaging data;
segmenting abnormality regions associated with a disease from the medical imaging data;
calculating a volume metric of the lungs based on the segmented lungs;
calculating a volume metric of the abnormality regions based on the segmented abnormality regions; and
determining an assessment of the disease based on the volume metric of the lungs and the volume metric of the abnormality regions, wherein determining an assessment of the disease based on the volume metric of the lungs and the volume metric of the abnormality regions comprises:
calculating a percent of opacity metric by dividing the volume metric of the lungs by the volume metric of the abnormality regions.

15. The non-transitory computer readable medium of claim 14, wherein the disease is COVID-19 (coronavirus disease 2019) and the abnormality regions associated with COVID-19 comprise opacities of one or more of ground glass opacities (GGO), consolidation, and crazy-paving pattern.

16. The non-transitory computer readable medium of claim 14, wherein determining an assessment of the disease based on the volume metric of the lungs and the volume metric of the abnormality regions comprises:
calculating a metric quantifying the disease based on the segmented lungs and the segmented abnormality regions; and
comparing the calculated metric with a metric quantifying the disease calculated based on prior medical imaging data acquired at a previous point in time than the medical imaging data.

17. The non-transitory computer readable medium of claim 14, wherein determining an assessment of the disease based on the volume metric of the lungs and the volume metric of the abnormality regions comprises:
classifying the disease as being one of COVID-19 (coronavirus disease 2019), SARS (severe acute respiratory syndrome), or MERS (middle east respiratory syndrome).

18. The non-transitory computer readable medium of claim 14, wherein determining an assessment of the disease based on the volume metric of the lungs and the volume metric of the abnormality regions comprises:
detecting presence of COVID-19 in the lungs based on the segmented lungs, the segmented abnormality regions, and patient data.

19. The non-transitory computer readable medium of claim 14, wherein the disease is a viral pneumonia.

20. A non-transitory computer readable medium storing computer program instructions, the computer program instructions when executed by a processor cause the processor to perform operations comprising:
receiving medical imaging data of lungs of a patient;
segmenting the lungs from the medical imaging data;
segmenting abnormality regions associated with a disease from the medical imaging data;

calculating a volume metric of the lungs based on the segmented lungs;

calculating a volume metric of the abnormality regions based on the segmented abnormality regions; and determining an assessment of the disease based on the volume metric of the lungs and the volume metric of the abnormality regions, wherein determining an assessment of the disease based on the volume metric of the lungs and the volume metric of the abnormality regions comprises:

calculating a percent of opacity metric for each lobe of the lungs based on a volume metric of each lobe determined from the segmented lungs and a volume metric of abnormality regions in each lobe determined from the segmented abnormality regions;

assigning each lobe with a score based on its percent of opacity metric; and summing the scores to calculate a lung severity score.

\* \* \* \* \*